United States Patent
Borens et al.

(10) Patent No.: US 8,863,552 B2
(45) Date of Patent: Oct. 21, 2014

(54) SINTERING OF FUSED SILICA TO PRODUCE SHAPED BODIES COMPRISING CRYSTALLINE $SIO_2$

(75) Inventors: Manfred Borens, Mainz (DE); Karsten von Westernhagen, Mainz (DE); Stefano Merolla, Mainz (DE); Gerald Wasem, Schmalfelderhof (DE); Stefan Postrach, Mainz (DE)

(73) Assignee: Schott AG (DE)

( * ) Notice: Subject to any disclaimer, the term of this patent is extended or adjusted under 35 U.S.C. 154(b) by 941 days.

(21) Appl. No.: 12/014,618

(22) Filed: Jan. 15, 2008

(65) Prior Publication Data

US 2008/0196448 A1    Aug. 21, 2008

(30) Foreign Application Priority Data

Jan. 23, 2007  (DE) .......................... 10 2007 004 242

(51) Int. Cl.
 *C03B 19/01*    (2006.01)
 (Continued)

(52) U.S. Cl.
 CPC ........... *C03C 3/06* (2013.01); *C04B 2235/6562* (2013.01); *C03B 19/066* (2013.01);
 (Continued)

(58) Field of Classification Search
 CPC .................. C04B 2235/3418; C04B 2235/96; C04B 14/06; C04B 2235/6027; C04B 2235/661; C04B 2235/5463; C04B 2235/72; C04B 2235/785; C04B 2235/786; C03B 5/43; C03B 19/1005; C03B 1/00; C03C 3/087
 USPC ........ 65/144, 17.1–17.4; 501/1–2, 4; 264/434
 See application file for complete search history.

(56) References Cited

U.S. PATENT DOCUMENTS 3,592,619 A * 7/1971 Thomas ............................ 65/22
3,949,030 A * 4/1976 Murata ........................... 264/43
(Continued)

FOREIGN PATENT DOCUMENTS

GB    1392227    4/1975
JP    63215600   8/1988
(Continued)

OTHER PUBLICATIONS

Translation of DE10244040 as provided by http://translationportal.epo.org/emtp/translate/?ACTION=description-retrieval&COUNTRY=DE&FORMAT=docdb&KIND=C1& LOCALE=en_GB&NUMBER=10244040&OPS=ops.epo.org& TRGLANG=en&ENGINE=google&SRCLANG=de viewed on Nov. 18, 2011.*

(Continued)

*Primary Examiner* — Jodi C Franklin
(74) *Attorney, Agent, or Firm* — Kaplan Breyer Schwarz & Ottesen, LLP (57) ABSTRACT

A process is disclosed for simple and rapid production of a shaped body comprising fused silica and a shaped body which leads to virtually no contamination of a melt in contact with the shaped body even at high temperatures. The disclosed process comprises the steps of: a) provision of fused silica in the form of essentially amorphous $SiO_2$ grains of which not more than 5% have a diameter greater than 15 mm, b) addition of water to the fused silica grains to produce a slip, c) casting of the slip into a mold which comprises a hollow body having the inverse shape of the shaped body to be produced, and d) drying of the slip to give an intermediate body, which is then sintered and cooled. A shaped body producible in accordance with the aforementioned process is also disclosed, which comprises at least 99.0 mol % of $SiO_2$.

15 Claims, 6 Drawing Sheets

(51) Int. Cl.

| | |
|---|---|
| *C03B 19/02* | (2006.01) |
| *C03B 19/06* | (2006.01) |
| *C04B 35/14* | (2006.01) |
| *C04B 35/626* | (2006.01) |
| *C03B 20/00* | (2006.01) |
| *C03C 3/06* | (2006.01) |
| *B82Y 5/00* | (2011.01) |
| *C03B 5/43* | (2006.01) |

(52) U.S. Cl.
CPC ........ C04B 2235/5427 (2013.01); *C03B 19/06* (2013.01); *C04B 35/14* (2013.01); *C04B 35/62665* (2013.01); *C03B 20/00* (2013.01); C04B 2235/6027 (2013.01); C04B 2235/72 (2013.01); C04B 2235/96 (2013.01); C04B 2235/6028 (2013.01); C04B 2235/9607 (2013.01); C04B 2235/95 (2013.01); *B82Y 5/00* (2013.01); *C03B 5/43* (2013.01); C04B 2235/5472 (2013.01); C04B 2235/77 (2013.01); C04B 2235/6565 (2013.01); C04B 2235/656 (2013.01)
USPC ............................... 65/17.3; 65/17.4; 65/17.5

(56) References Cited

U.S. PATENT DOCUMENTS

| | | | | |
|---|---|---|---|---|
| 3,991,234 | A * | 11/1976 | Chang et al. ................. | 427/164 |
| 4,072,489 | A * | 2/1978 | Loxley et al. ................. | 65/17.3 |
| 4,429,009 | A * | 1/1984 | Pastor et al. ................. | 428/410 |
| 4,853,198 | A * | 8/1989 | Orii et al. ..................... | 423/335 |
| 5,028,407 | A * | 7/1991 | Chieng et al. ................ | 423/338 |
| 5,053,359 | A | 10/1991 | Loxley | |
| 5,063,003 | A * | 11/1991 | Gonzalez-Oliver ............. | 264/14 |
| 5,360,773 | A * | 11/1994 | Winkelbauer et al. ........ | 501/133 |
| 5,389,582 | A * | 2/1995 | Loxley et al. ..................... | 501/4 |
| 5,849,055 | A * | 12/1998 | Arai et al. ..................... | 65/17.3 |
| 5,972,488 | A * | 10/1999 | Nagata et al. ............. | 428/304.4 |
| 6,012,304 | A * | 1/2000 | Loxley et al. .................. | 65/111 |
| 6,355,587 | B1 * | 3/2002 | Loxley et al. .................. | 501/54 |
| 6,381,986 | B1 * | 5/2002 | Loxley et al. ................. | 65/17.5 |
| 8,104,309 | B2 * | 1/2012 | Borens et al. ................ | 65/17.3 |
| 2002/0108399 | A1 * | 8/2002 | Bhandarkar et al. ........... | 65/17.2 |
| 2002/0152768 | A1 * | 10/2002 | Loxley et al. ................. | 65/17.2 |
| 2007/0082149 | A1 * | 4/2007 | Linnot et al. ................ | 428/34.4 |
| 2008/0196448 | A1 * | 8/2008 | Borens et al. ................ | 65/17.1 |

FOREIGN PATENT DOCUMENTS

| | | | | |
|---|---|---|---|---|
| JP | 05262513 | A * | 10/1993 | .............. C01B 33/18 |
| WO | WO2005016837 | | * 2/2005 | .............. C03B 19/06 |

OTHER PUBLICATIONS

Dr. Feigl, "German Patent Application No. 10 2007 004 242.8", May 22, 2009, Publisher: Deutsches Patent- und Markenamt, Published in: DE.

D Kicevit, M. Gasic, "A Statistical Analysis of the Influence of Processing Conditions on the Properties of Fused Silica", "Journal of the European Ceramic Society", 1996, Publisher: Elsevier Science, Ltd., Published in: GB.

"Chinese Office Action for Chinese International Application No. 200810215450.7", Dated: Feb. 23, 2011, Publisher: Chinese Patent Office, Published in: CN.

* cited by examiner

SINTERING OF FUSED SILICA TO PRODUCE SHAPED BODIES COMPRISING CRYSTALLINE SIO₂

FIELD OF THE INVENTION

The invention relates to a process for producing a shaped body comprising fused silica by sintering, a shaped body and the use of such a shaped body.

BACKGROUND OF THE INVENTION

Specifically, the invention relates to the processing of melts of glass, metals, semimetals and similar materials at high temperatures of several 100° C. The processing can comprise, for example, production of a melt of raw material, in the case of glass especially crushed glass and/or mechanical mixtures, and also refining, homogenization and further steps such as passing to shaping. In all such process steps, use is made of vessels such as crucibles, melting tanks, refining tanks, pipes, stirrers and other apparatuses of which areas come into contact with the melt during operation.

A material for such components has to have a high resistance to chemical attack as a result of contact with the melt, i.e. a high corrosion resistance, so that contamination of the melt by introduction of particles of the material is largely avoided.

In DE 102 44 040, the applicant proposes a sintered silica material which has a two-layer structure for glass production. Cristobalite is a crystal modification of $SiO_2$ and offers the advantage of higher corrosion resistance than amorphous fused silica. According to DE 102 44 040, care has to be taken in the production of the material by slip casting of fused silica particles to ensure that no or only little cristobalite is formed, since beta-cristobalite transforms into alpha-cristobalite at about 270° C. with a volume decrease of at least 2%. This volume change is considered as destructive to the component.

To be able to utilize the high corrosion resistance of crystalline $SiO_2$ during use of the component, the particle size of the $SiO_2$ grains is, at least in the outer region of the component, selected so that cristobalite formation occurs more quickly than removal of material from the surface of the fused silica as a result of corrosion during operation. An outer layer of the material for use in contact with a glass melt comprises fused silica grains having a diameter of less than 40 microns. These small fused silica grains are used so that very rapid devitrification of the fused silica with conversion into cristobalite occurs during operation at appropriately high temperatures.

However, the production of a two-layer shaped body is labour-intensive and therefore costly. In addition, the sintering process has to be carried out at sufficiently low temperatures for crystallization to be largely avoided. The sintering process is therefore time-consuming. Furthermore, when the shaped body is used in contact with a melt during operation at high temperatures, the shrinkage which then occurs as a result of transformation of the amorphous fused silica into crystalline modifications has to be taken into account.

SUMMARY OF THE INVENTION

It is therefore an object of the invention to provide a simple and rapid process for producing a shaped body comprising fused silica by sintering. A further object of the invention is to provide a shaped body which even at high temperatures leads to virtually no contamination of a melt which is in contact with the shaped body.

The invention provides a process for producing a shaped body, which comprises the steps:
a) provision of fused silica in the form of essentially amorphous $SiO_2$ grains of which 5%, preferably not more than 3%, particularly preferably not more than 2%, have a diameter greater than 15 mm, preferably greater than 10 mm, particularly preferably greater than 6 mm,
b) addition of water to the fused silica grains to produce a slip,
c) casting of the slip into a mould which comprises a hollow body having the inverse shape of the shaped body to be produced,
d) drying of the slip to give an intermediate body,
e) sintering of the intermediate body at a sintering temperature at which at least part of the fused silica is transformed from the amorphous modification into a crystalline modification, in particular beta-cristobalite,
f) cooling of the sintered shaped body to a temperature below 300° C., preferably below 270° C., so that a microstructure containing crystalline $SiO_2$ is formed.

For Example, the procedures described in more detail below can be employed in further individual steps.

Surprisingly and contrary to what DE 102 44 04 would lead one to expect, the shaped body is not destroyed by the cooling process after firing, although cristobalite is formed during production of the component. The transformation of beta-cristobalite into alpha-cristobalite is associated with a volume decrease of from 2 to 2.8%. However, even when, according to the invention, no stabilizers are added and the purity of the material is advantageously maintained, the shaped body according to the invention remains stable and can be processed further without problems, since the size prescribed according to the invention of the fused silica grains used leads to a microstructure in the sintered shaped part which tolerates the stresses arising during the transformation between the crystal modifications.

The invention therefore offers the advantage of the improved corrosion resistance, in particular to glass melts, because, due to crystal formation during production, the transformation of amorphous into crystalline $SiO_2$ commences more quickly in later use of the component since crystal nuclei have already been incorporated during production.

In step c), it is possible to use, for example, a plaster mould. The surfaces of the mould which come into contact with the shaped part can be machined according to requirements for the surface quality of the component to be produced. Firing of the intermediate body for the purpose of sintering in step e) can also be carried out after removal of the intermediate body from the mould. Depending on how the external shape of the intermediate body is configured and the stresses, for example as a result of its own weight, the intermediate body has to withstand as a result, presintering in the mould can be carried out.

In a preferred embodiment of the invention, essentially pure fused silica in amorphous form having an $SiO_2$ content of at least 99.0% by weight, preferably at least 99.5% by weight, particularly preferably at least 99.9% by weight, is used in step a). The $SiO_2$ used in step a) can contain up to 3% of crystalline $SiO_2$.

Preference is given to using essentially alkali-free water in step b).

The sintering of the intermediate body in step e) can, according to the invention, be carried out at relatively high temperatures so that not only are material bridges between the fused silica grains formed but crystal formation also commences. Sintering is normally carried out at a temperature of at least 1080° C., preferably at least 1120° C., more preferably at least 1140° C., particularly preferably at least 1180° C.

Due to the high sintering temperature according to the invention, regulation of the furnace can also be simplified and/or the firing time can be shortened significantly compared to firing at sintering temperatures of not more than 1000° C. In addition, better sintering of the grains occurs, which results in a lower residual porosity after firing, a higher density, a better mechanical stability and a lower shrinkage due to after-sintering effects during later use of the component.

In a preferred embodiment of the invention, the maximum temperature during sintering is, depending on the dimensions of the intermediate body, selected so that the shaped body to be produced attains a homogeneous internal structure due to sintering of the fused silica and at the same time crystal formation advantageously occurs to the desired extent in the exterior regions of the shaped body. According to the findings of the inventors, a maximum temperature during sintering of, for example, about 1285° C. at a maximum wall thickness of the intermediate body of less than or equal to about 85 mm has been found to be suitable. At a maximum wall thickness of the intermediate body of more than about 85 mm, this temperature can be reduced, for example, to about 1250° C.

The process of the invention makes it possible to obtain a shaped body which consists virtually entirely of $SiO_2$ and has embedded crystals. During later use of the shaped body in contact with a very hot material, for example a glass melt, the embedded crystals can serve as nuclei for further crystal growth in the form of cristobalite which has a higher corrosion resistance than amorphous fused silica. Particularly advantageous properties of the shaped body of the invention are the higher density and lower porosity associated with the content of crystalline $SiO_2$. These additionally contribute to the mechanical stability of the component without additives such as pure silicon powder having to be used.

The invention accordingly provides a shaped body which, in particular, can be produced or is produced by a process as described above and comprises at least 99.0 mol %, preferably at least 99.5 mol %, particularly preferably at least 99.9 mol %, of $SiO_2$.

In a preferred embodiment of the invention, the outer layer of the shaped body, which has a thickness of up to 40 mm measured from the surface, has a content of crystalline $SiO_2$, in particular cristobalite, averaged over its thickness in the range from 2% by volume to 5% by volume, preferably from 2.5% by volume to 4.5% by volume, particularly preferably 2.9% by volume±0.1% by volume.

The content of crystalline $SiO_2$ can be measured at room temperature as alpha-cristobalite by means of X-ray diffraction.

To achieve a particularly high corrosion resistance of the shaped body when used in contact with very hot media without volume changes leading to cracks in the shaped body occurring during temperature changes, for example as a result of phase transitions, the shaped body of the invention is provided with an increased content of crystalline $SiO_2$, especially in the regions close to the surface.

In an advantageous embodiment, the outer layer of the shaped body, which has a thickness of up to 20 mm measured from the surface, has a content of crystalline $SiO_2$, in particular cristobalite, averaged over the thickness in the range from 2.3% by volume to 5.5% by volume, preferably in the range from 3.0% by volume to 5.5% by volume, particularly preferably from 3.5% by volume to 4.5% by volume, particularly preferably 3.75% by volume±0.1% by volume.

Particular preference is given to a shaped body whose outer layer, which has a thickness of up to 10 mm measured from the surface, has a content of crystalline $SiO_2$, in particular cristobalite, averaged over the thickness in the range from 2.3% by volume to 6.5% by volume, preferably in the range from 3.5% by volume to 6.5% by volume, particularly preferably from 4% by volume to 5% by volume, particularly preferably 4.6% by volume±0.1% by volume. An advantageous embodiment provides for the outer layer of the shaped body, which has a thickness of up to 5 mm measured from the surface, to have a content of crystalline $SiO_2$, in particular cristobalite, averaged over the thickness in the range from 2.3% by volume to 7.5% by volume, preferably in the range from 4.0% by volume to 7.5% by volume, particularly preferably from 4.5% by volume to 6.5% by volume, particularly preferably 5.1% by volume±0.1% by volume.

In a preferred embodiment, the outer layer of the shaped body, which has a thickness of up to 2 mm measured from the surface, has a content of crystalline $SiO_2$, in particular cristobalite, averaged over the thickness in the range from 2.3% by volume to 8.0% by volume, preferably in the range from 4.3% by volume to 8.0% by volume, particularly preferably from 4.8% by volume to 6.8% by volume, particularly preferably 5.3% by volume±0.1% by volume. The outer layer of the shaped body, which has a thickness of up to 1 mm measured from the surface, advantageously has a content of crystalline $SiO_2$, in particular cristobalite, averaged over the thickness in the range from 2.5% by volume to 8.5% by volume, preferably in the range from 4.5% by volume to 8.5% by volume, particularly preferably from 5% by volume to 6.3% by volume, particularly preferably 5.4% by volume±0.1% by volume.

A preferred embodiment provides for the outer layer of the shaped body, which has a thickness of up to 0.3 mm measured from the surface, to have a content of crystalline $SiO_2$, in particular cristobalite, averaged over the thickness in the range from 2.7% by volume to 9.5% by volume, preferably in the range from 4.7% by volume to 9.5% by volume, particularly preferably from 5.1% by volume to 6.8% by volume, particularly preferably 5.5% by volume±0.1% by volume. Particular preference is given to a shaped body which, in a layer which is located between a depth of 20 mm and a depth of up to 40 mm, measured from the surface of the shaped body, and thus has a thickness of up to 20 mm, has a content of crystalline $SiO_2$, in particular cristobalite, averaged over the thickness in the range from 1% by volume to 3% by volume, preferably from 1.5% by volume to 2.5% by volume, particularly preferably 2% by volume±0.1% by volume.

Apart from the content of crystalline phase to increase the corrosion resistance of the shaped body, the shaped body also advantageously has, according to the invention, an improved mechanical stability. Thus, the density of sintered silica material produced by slip casting is generally in the range from 1.80 to 2.05 g/cm³. However, according to the invention, a higher density can be achieved as a result of the higher firing temperature and the deliberate formation of cristobalite during sintering. The shaped body of the invention has, at least in a region, in particular in a region of its outer layer which has a thickness of up to 20 mm measured from the surface of the shaped body, a density averaged over the thickness in the range from 1.92 g/cm³ to 2.12 g/cm³.

The open porosity of sintered silica material produced by slip casting is in the range from 10.5 to 15% by volume. The production process of the invention produces, in particular, a shaped body which, at least in a region, in particular in a region of its outer layer which has a thickness of up to 20 mm measured from the surface of the shaped body, has an open porosity averaged over the thickness in the range below 12%, preferably below 9%, particularly preferably 7.5%.

The properties of the shaped body of the invention make it particularly suitable for use as crucible or part of a crucible for use in contact with a melt of at least one metal and/or semi-metal and/or semiconductor and/or glass. As for a crucible, the invention provides for the use of the shaped body for a melting tank and/or a refining tank and/or a pipe and/or a stirrer and/or another apparatus used in the processing of melts.

BRIEF DESCRIPTION OF THE DRAWINGS

The invention is illustrated below with the aid of examples and with reference to the accompanying drawings. In the drawings.

DETAILED DESCRIPTION

Figure 1:
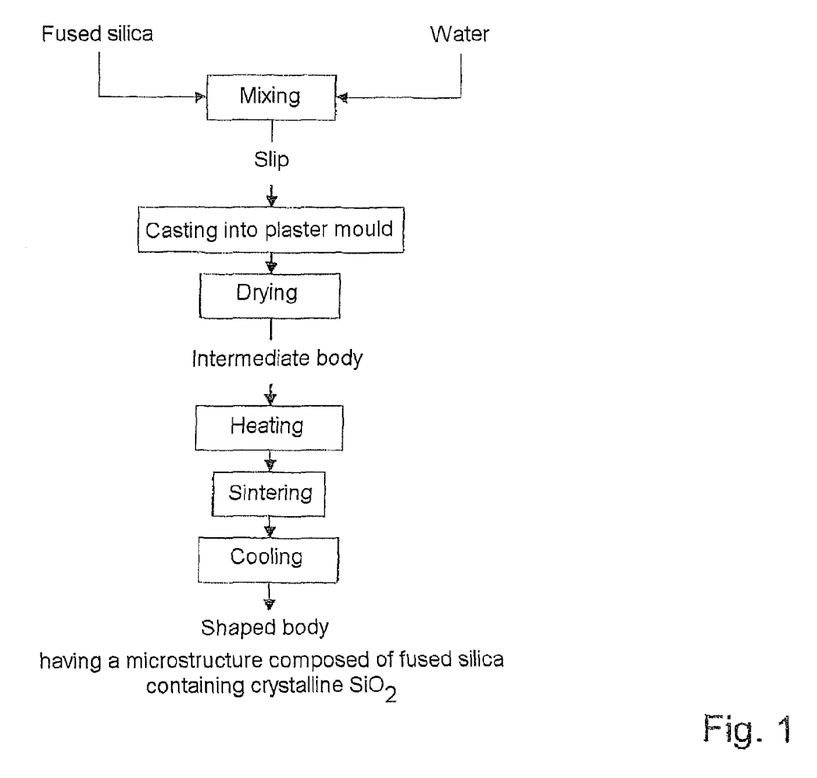
FIG. 1 shows a schematic flow diagram of the process.

To produce a shaped body having a microstructure comprising sintered, amorphous fused silica grains in which $SiO_2$ in crystalline form, in particular in the form of cristobalite, is embedded, a slip is produced by mixing fused silica grains with water (see FIG. 1).

Pure fused silica is used for the slip. No stabilizer such as phosphate is added in order to suppress cristobalite formation. Various classes of purity of the fused silica are possible, namely at least 99.0% of $SiO_2$, better at least 99.5% of $SiO_2$, and fused silica having a purity of at least 99.9% by weight of $SiO_2$ is particularly suitable. The remaining constituents are metal oxides which are introduced with the raw material (fused silica) or get into the product during processing by contact with the materials of construction of the plants. Examples of such metal oxides are $Al_2O_3$, $Na_2O$, Fe oxides, TiO and others. Further impurities can be introduced by the water used (e.g. Na, Mg, Ca salts).

The pure fused silica is milled and various particle size fractions are then separated. For the components mentioned here, grains or fragments having a size above 8 mm are sieved out. Although a small proportion, up to about 2%, of grains having an average diameter above 8 mm do not have a harmful effect on the behaviour of the material, at a proportion above 2% the flowability of the slip is adversely affected. The production of thin-walled components having wall thicknesses below 25 mm is then possible only with extreme difficulty. Since the larger grains bring no advantage, they are therefore preferably sieved out completely.

Alkali-free water is used for the slip. In the slip, the fused silica grains have a water layer on their surface, with the ratio of fused silica to water being set so that the slip has a non-newtonian, in particular rheopexic, flow behaviour.

The slip is poured into a plaster mould. The plaster mould takes up water from the slip, so that drying of the body of slip occurs even in the plaster mould. Drying can be carried out at room temperature under atmospheric pressure solely by means of the ongoing water absorption by the plaster mould until a sufficiently stable intermediate body has been produced. Drying can be accelerated by increasing the temperature and/or reducing the pressure.

The intermediate body is then heated to a temperature at which the fused silica grains sinter and partial conversion of the amorphous phase into a crystalline phase occurs. The body is subsequently cooled. The end product of the production process is a shaped body having a microstructure composed of fused silica containing crystalline $SiO_2$.

The sintering temperature or firing temperature is above 1080° C., better above 1120° C. Preference is given to a sintering temperature or firing temperature of above 1140° C., even better above 1180° C. The maximum temperature during firing is selected as a function of the maximum wall thickness of the component. A maximum firing temperature of 1250° C. has been found to be suitable at maximum wall thicknesses of more than 85 mm and a maximum firing temperature of 1285° C. has been found to be appropriate at maximum wall thicknesses of less than or equal to 85 mm.

Figure 2:
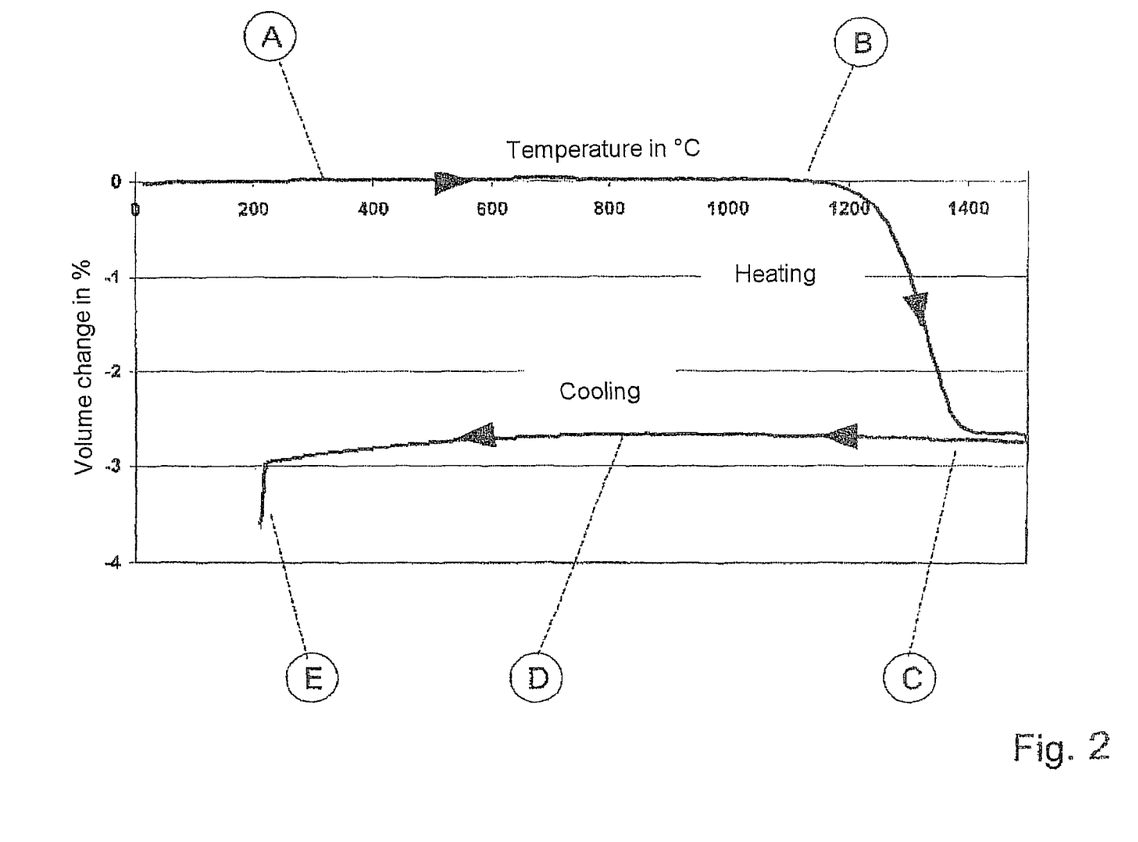
FIG. 2 shows a plot of the length change on heating and cooling of the sintered silica material during production of the shaped body, FIG. 3 schematically shows an enlarged section X of a shaped body.

In FIG. 2, the volume change in the shaped body associated with the temperature profile during heating, sintering and cooling is plotted. The individual steps carried out are shown in the following table:

| | Description | Remarks |
|---|---|---|
| Step 1 | From room temperature to 90° C.-120° C. at 10-30 K/min | |
| Step 2 | Hold time (depending on wall thickness) from 12 hours to 96 hours | Drying |
| Step 3 | Further heating at 1 K/min-30 K/min to 1030° C.-1230° C. | If appropriate insert further hold times as a function of the wall thickness; e.g.: 24 hours at 300° C. |
| Step 4 | Hold time (depending on wall thickness) from 0.25 hour to 24 hours | |
| Step 5 | Further heating to the maximum firing temperature in the range from 1100° C. to 1285° C. at about 1 K/min | In exceptional cases: Maximum temperature up to 1320° C. |
| Step 6 | Hold time at the maximum temperature of from 1 hour to 32 hours | |
| Step 7 | Cooling to 380° C.; maximum cooling rate: 350 K/min | Can be carried out without regulation/ switching off the heating power; cooling rate is determined by the heat loss (for example depending on the furnace insulation) |
| Step 8 | Hold time; depending on the wall thickness; maximum 4 hours | For components having a wall thickness below 40 mm: no hold time; at a wall thickness of >120 mm: 4 hours |
| Step 9 | Cooling to 250° C.; cooling rate: in the range from 1 K/min to 25 K/min | |
| Step 10 | Hold time depending on the wall thickness; maximum 1 hour | For components having a wall thickness below 40 mm: no hold time; at a wall thickness of >120 mm: 4 hours |

| Description | Remarks |
|---|---|
| Step 11 | Cooling to room temperature; no regulated cooling necessary; component can be taken from the furnace immediately |

During heating, the thermal expansion is negligible up to a temperature of about 1000° C. The volume remains virtually constant during heating (region A in the graph).

Above about 1000° C., sintering of the amorphous fused silica grains commences; above about 1100° C., transformation of the amorphous glass phase into crystalline beta-cristobalite occurs. This is associated with a reduction in volume (region B). Heating for sintering and crystal formation is continued up to a temperature above 1300° C.

As soon as sintering and transformation into the crystalline modification has occurred to the desired extent, the component is cooled (from region C). The component produced by this process can be used without changes even at very high temperatures up to its melting point. Cooling down to a temperature of about 270° C. occurs without a significant volume change (region D). Below about 270° C., beta-cristobalite is transformed into alpha-cristobalite with an immediate decrease in volume of about 3% (region E).

Figure 3:
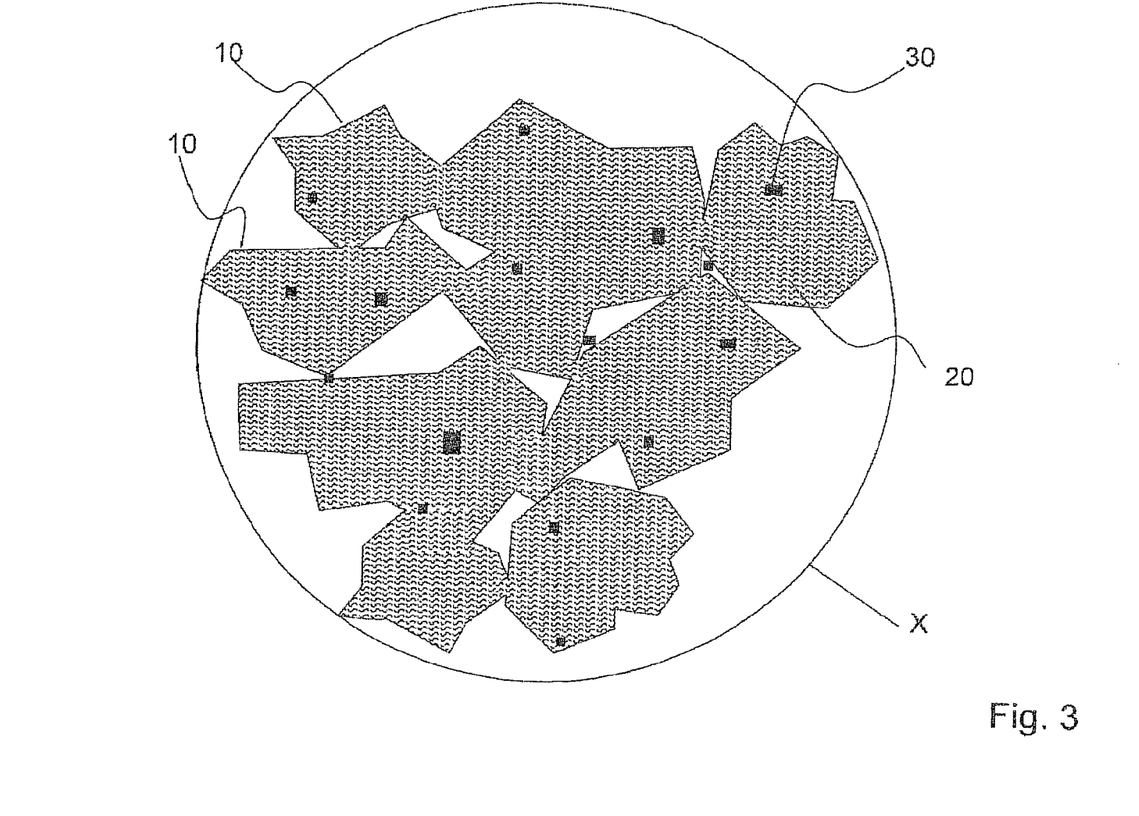

FIG. 3 schematically shows an enlarged section X of the resulting microstructure of the shaped body. Grains 10 are joined to one another via sintered bridges to form a stable solid. The grains comprise amorphous fused silica 20. $SiO_2$ crystals 30 are embedded in the microstructure. These can be present in the interior of a grain and/or at places where the grains abut and/or in surface regions of the grains which go over into voids of the microstructure.

Figure 4:
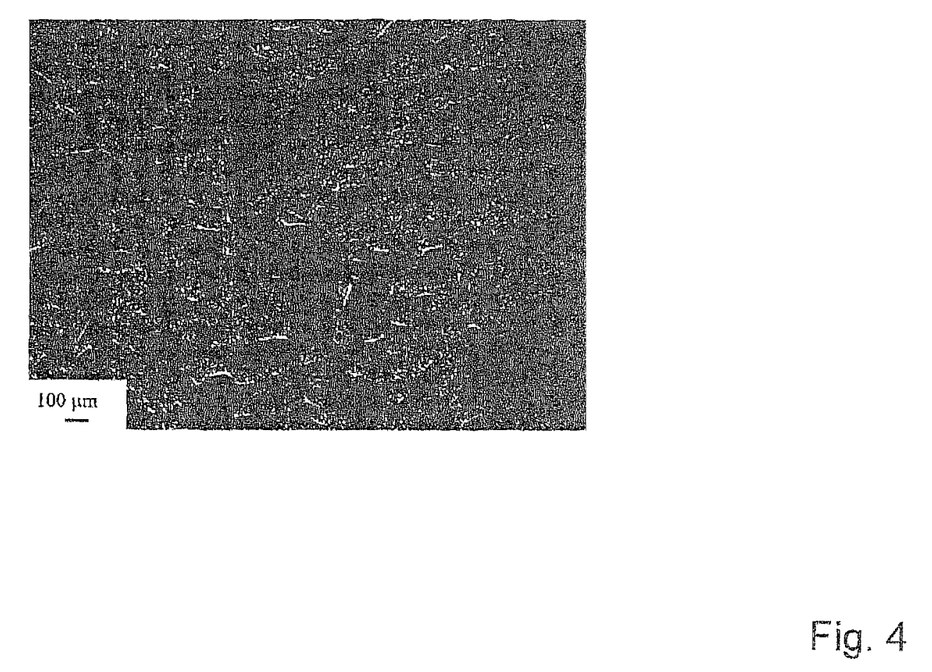
FIG. 4 shows a photomicrograph of a polished section of a shaped body having a cristobalite content according to the invention.
Figure 5:
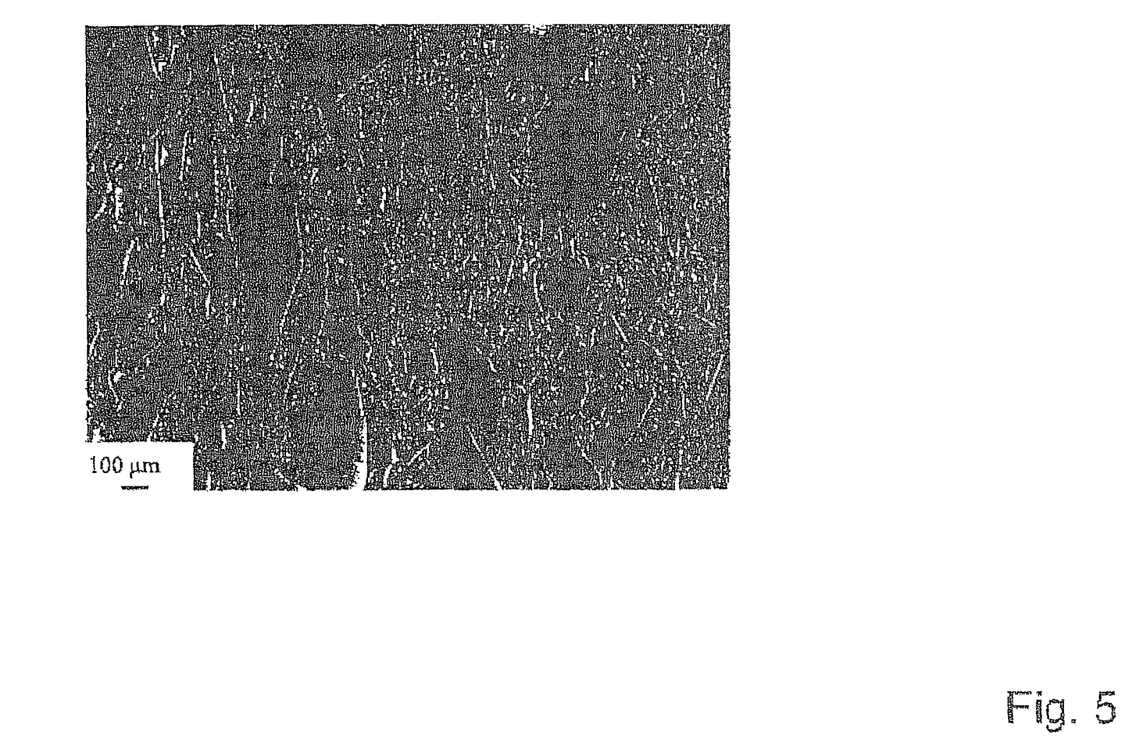
FIG. 5 shows a photomicrograph of a polished section of a shaped body which has been sintered with a conventional temperature profile and FIG. 6 schematically shows a shaped body.

FIG. 4 shows a polished section of a microstructure after sintering in the temperature range with commencement of cristobalite formation. The overall density of the material is 1.95 g/cm³; its open porosity is 11.0%. The cristobalite content itself cannot be determined optically from the polished section. For comparison, FIG. 5 shows a polished section of a microstructure which has been produced by standard sintering. The overall density of this material is 1.84 g/cm³; its open porosity is 13.3%.

Figure 6:
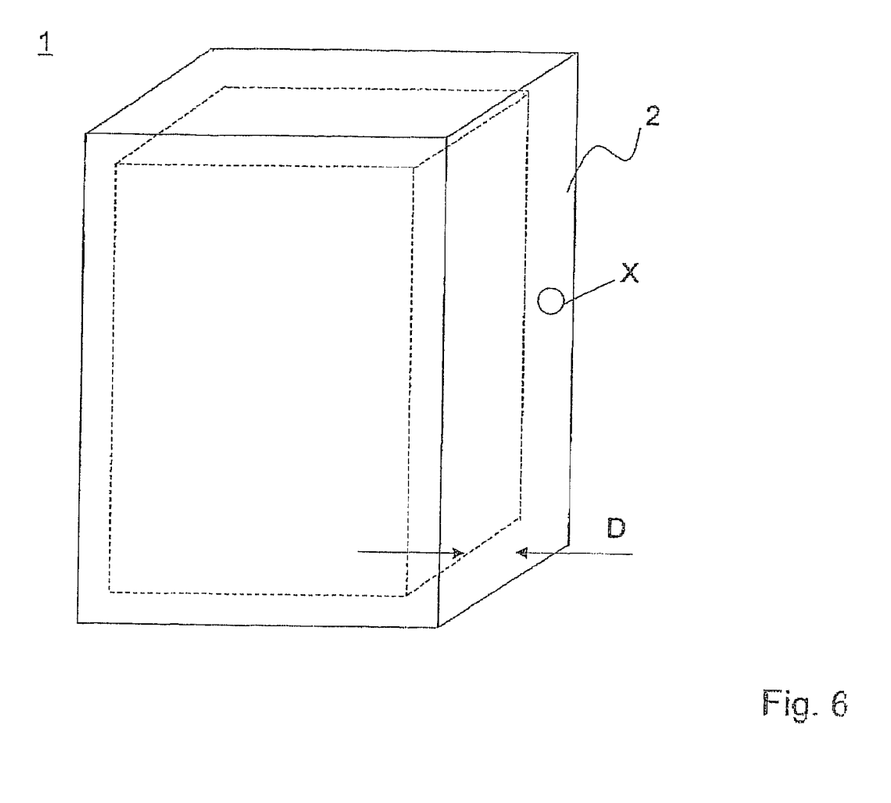

FIG. 6 schematically shows a shaped body 1. The shaped body 1 has an outer region 2 having a thickness D. At least in the outer region 2, the shaped body 1 has a microstructure as illustrated in FIG. 3.

The shaped body has an improved corrosion resistance towards glass melts because transformation in later use commences more quickly due to initial cristobalite formation during production. Cristobalite is more resistant to corrosion by glass than is fused silica.

To determine the corrosion resistance, the following corrosion test in the presence of borosilicate glass 3.3 was carried out in accordance with ISO 3585 and EN 1595. Glass having the following composition was used:
81% of silica ($SiO_2$),
13% of boric acid ($B_2O_3$),
4% of alkalis ($Na_2O$; $K_2O$) and
2% of other constituents (for example $Al_2O_3$).

In a static corrosion test, specimens of the material of the shaped body according to the invention are suspended in the glass melt. Both the glass melt and the specimen are kept stationary. The time of the test is 168 hours at a test temperature of 1400° C. After the test time has elapsed, the removal of material from the surface of the specimens is measured in comparison with the dimensions of the specimen at the beginning of the test.

The removal of material from a specimen having a proportion of crystalline $SiO_2$ is significantly lower than in the case of a specimen of conventional material which does not have a proportion of crystalline $SiO_2$ at the beginning of the test. At the temperature of 1400° C., the crystalline $SiO_2$ is present in the form of cristobalite.

The removal of material from a cristobalite-containing specimen is on average 0.77 mm; individual values in the range from 0.71 mm to 0.82 mm were measured. The removal of material from a comparative specimen without a proportion of cristobalite at the commencement of the test is on average 1.05 mm; individual values in the range from 1.0 mm to 1.1 mm were measured.

At the temperature of 1400° C., cristobalite is also formed in the comparative specimen. However, the specimen of the material according to the invention has a proportion of cristobalite at the surface even at the beginning of the test. At the end of the test, the material of both specimens has been converted virtually completely into cristobalite; the residual glass content is less than 10%.

Apart from the increased corrosion resistance, the production process is also simplified by the invention since a higher sintering temperature can be utilized. This results in simpler furnace regulation, and the firing time can also be shortened because of the higher temperatures. Since the firing temperature is increased in the production of the components and better sintering can therefore be achieved, the residual porosity is reduced and the density and the mechanical stability of the components are increased.

In addition, the shrinkage during later use as a result of after-sintering effects is lower. If the use temperatures are above the firing temperatures, the material can shrink as a result of the ongoing sintering process. Since a higher overall density or lower residual porosity of the material is achieved according to the invention by means of the production process alone, the shrinkage is significantly reduced in the case of the material according to the invention compared to known materials.

For a material sintered without commencement of cristobalite formation, the shrinkage in later use is in the range from 2.0% to 4%. The shrinkage is very strongly influenced by the particle size distribution of the starting material for production of the slip and by the firing temperature. If the firing temperature is, as described above, made so high that the region of cristobalite formation is reached, the shrinkage can be reduced to 1.0-2.0%.

Example of a Material Having the Following Particle Size Distribution of the Starting Material:

| Proportion [% by weight] | Particle size |
|---|---|
| 40 to 60 | less than 0.3 mm |
| 20 to 30 | 0.3 mm to 1.0 mm |
| 20 to 30 | 1.0 mm to 6.0 mm |

In the case of normal sintering without the cristobalite formation zone being reached, the shrinkage is on average from 2.5% to 3%. Sintering with commencement of cristobalite formation enables the shrinkage to be reduced to less than 1.5% (for example to 1.0-1.5%).

The denser presintering also leads to a higher mechanical strength of the material and to a better thermal conductivity.

In the case of a material having the abovementioned particle size distribution in the starting raw material, the following values are obtained:

| | Material without cristobalite | Presintered with commencement of cristobalite formation |
|---|---|---|
| Cold flexural strength (room temperature) [MPa] | 14 | 23 |
| Modulus of elasticity (room temperature) [GPa] | 18 | 30 |
| Hot flexural strength (900° C.) [MPa] | 20 | 46 |
| Modulus of elasticity (at 900° C.) [GPa] | 26 | 47 |
| Thermal conductivity [W/mK] at 150° C. | 1.04 | 1.4 |
| Thermal conductivity [W/mK] at 550° C. | 1.24 | 1.6 |
| Density [kg/m$^3$] | 1960 | 2015 |

The values reported are average values derived from a plurality of measurements. Individual values can deviate therefrom. The wall thickness of the body from which the specimens were cut was 40 mm.

A person skilled in the art will be able to see that the invention is not restricted to the above-described examples but can be varied in a variety of ways. In particular, the features of the individual examples can also be combined with one another.

The invention claimed is:

1. A process for producing a shaped body, comprising:
   a) providing fused silica in amorphous form having an SiO$_2$ content of at least 99.5% by weight in the form of essentially amorphous SiO$_2$ grains of which not more than 5% have a diameter greater than 15 mm, wherein the proportion [% by weight] of particle size<0.3 mm is between 40% and 60% and the proportion [% by weight] of particle size 0.3 mm to 1.0 mm is between 20% and 30% and the proportion [% by weight] of particle size 1.0 mm to 6.0 mm is between 20% and 30%,
   b) adding substantially alkali-free water to the fused silica grains to produce a slip without any stabilizers, with a ratio of fused silica grains to water being set so that the slip has a nonnewtonian and rheopexic flow behavior,
   c) casting the slip into a mould which comprises a hollow body having the inverse shape of the shaped body to be produced,
   d) drying the slip to give an intermediate body,
   e) sintering the intermediate body at a sintering temperature at which at least part of the fused silica is transformed from the amorphous modification into a crystalline modification, and
   f) cooling the sintered shaped body to a temperature below 300° C. so that a microstructure containing crystalline SiO$_2$ is formed.

2. The process according to claim 1, wherein the sintering temperature in step e) is at least 1080° C.

3. The process according to claim 1, wherein temperature applied during sintering in step e) is a maximum of 1285° C.

4. The process according to claim 1, wherein temperature applied during sintering in step e) is a maximum of 1250° C.

5. A shaped body produced by a process according to claim 1, wherein the cooling of the sintered shaped body results in the shaped body comprising at least 99.5% mol % of SiO$_2$.

6. The shaped body according to claim 5, wherein the sintering of the intermediate body is performed in such a way that the outer layer of the shaped body, which has a thickness of up to 40 mm measured from the surface, has a content of crystalline SiO$_2$ averaged over its thickness in the range from 2% by volume to 5% by volume.

7. The shaped body according to claim 5, wherein the sintering of the intermediate body is performed in such a way that the outer layer of the shaped body, which has a thickness of up to 20 mm measured from the surface, has a content of crystalline SiO$_2$ averaged over the thickness in the range from 2.3% by volume to 5.5% by volume.

8. The shaped body according to claim 5, wherein the sintering of the intermediate body is performed in such a way that the outer layer of the shaped body, which has a thickness of up to 10 mm measured from the surface, has a content of crystalline SiO$_2$ averaged over the thickness in the range from 2.3% by volume to 6.5% by volume.

9. The shaped body according to claim 5, wherein the sintering of the intermediate body is performed in such a way that the outer layer of the shaped body, which has a thickness of up to 5 mm measured from the surface, has a content of crystalline SiO$_2$ averaged over the thickness in the range from 2.3% by volume to 7.5% by volume.

10. The shaped body according to claim 5, wherein the sintering of the intermediate body is performed in such a way that the outer layer of the shaped body, which has a thickness of up to 2 mm measured from the surface, has a content of crystalline SiO$_2$ averaged over the thickness in the range from 2.3% by volume to 8.0% by volume.

11. The shaped body according to claim 5, wherein the sintering of the intermediate body is performed in such a way that the outer layer of the shaped body, which has a thickness of up to 1 mm measured from the surface, has a content of crystalline SiO$_2$ averaged over the thickness in the range from 2.5% by volume to 8.5% by volume.

12. The shaped body according to claim 5, wherein the sintering of the intermediate body is performed in such a way that the outer layer of the shaped body, which has a thickness of up to 0.3 mm measured from the surface, has a content of crystalline SiO$_2$ averaged over the thickness in the range from 2.7% by volume to 9.5% by volume.

13. The shaped body according to claim 5, wherein the sintering of the intermediate body is performed in such a way that the shaped body has, in a layer which is located between a depth of 20 mm and a depth of up to 40 mm, measured from the surface of the shaped body, and thus has a thickness of up to 20 mm, a content of crystalline SiO$_2$ averaged over the thickness in the range from 1% by volume to 3% by volume.

14. The shaped body according to claim 5, wherein the sintering of the intermediate body is performed in such a way that the shaped body has, at least in a region which has a thickness of up to 20 mm measured from the surface of the shaped body, a density averaged over the thickness in the range from 1.92 g/cm$^3$ to 2.12 g/cm$^3$.

15. The shaped body according to claim 5, wherein the sintering of the intermediate body is performed in such a way that the shaped body has, at least in a region, an open porosity averaged over the thickness in the range below 12%.

* * * * *